(12) United States Patent
Krantz et al.

(10) Patent No.: US 6,403,324 B1
(45) Date of Patent: Jun. 11, 2002

(54) AFFINITY LABELING LIBRARIES WITH TAGGED LEAVING GROUP

(75) Inventors: Alexander Krantz, Menlo Park; Arthur M. Hanel, San Francisco; Wolin Huang, Foster City, all of CA (US)

(73) Assignee: ConjuChem, Inc., Montreal (CA)

( * ) Notice: Subject to any disclaimer, the term of this patent is extended or adjusted under 35 U.S.C. 154(b) by 0 days.

(21) Appl. No.: 09/042,234

(22) Filed: Mar. 13, 1998

Related U.S. Application Data (63) Continuation-in-part of application No. 08/714,754, filed on Sep. 16, 1996, now abandoned.

(51) Int. Cl.[7] .......................... G01N 33/53; C12Q 1/00; A61K 38/00
(52) U.S. Cl. ............................. 435/7.1; 435/7.5; 435/4; 435/DIG. 1; 435/DIG. 2; 435/DIG. 14; 435/DIG. 15; 436/518; 530/300; 530/326
(58) Field of Search .......................... 435/4, 7.1, 6, 7.5, 435/DIG. 1, DIG. 2, DIG. 14, DIG. 15; 530/300, 350, 326, 412; 436/518

(56) References Cited

U.S. PATENT DOCUMENTS

| 5,438,119 A | 8/1995 | Rutter et al. |
| 5,510,240 A | 4/1996 | Lam et al. |
| 5,571,681 A | 11/1996 | Janda |
| 5,723,584 A | * 3/1998 | Schatz ....................... 530/408 |

FOREIGN PATENT DOCUMENTS

| EP | 0 639585 A1 | 8/1994 | ............ C07K/5/06 |
| EP | 0 742438 A2 | 4/1996 | .......... G01N/33/68 |
| WO | WO 95/34575 | 12/1995 | ............ C07K/1/04 |
| WO | WO 96/24061 | 8/1996 | ......... G01N/33/543 |

OTHER PUBLICATIONS

Schelhaas, M. et al.; Protecting Group Strategies in Organic Synthesis, Angew.Chem, Int. Ed. Engl. vol. 35, pp. 2056–2083 (1996).

* cited by examiner

*Primary Examiner*—Padmashri Ponnaluri
(74) *Attorney, Agent, or Firm*—Morrison & Foerster LLP (57) ABSTRACT

Methods and compositions are provided for identifying compounds having affinity to a target site. The method provides for the affinity group to be a leaving group from a reactive functionality capable of forming a covalent bond to the target site. One can combine the compound comprising the target site with the library, and assay for the resulting composition of the leaving groups. The leaving groups having the highest concentration can be identified as the groups having the binding highest affinity for the target site. The selected compounds may then be used for labeling the target molecule, particularly where the target molecule is naturally found in a complex mixture, such as a physiological fluid, like blood. By affinity labeling in vivo, the lifetime of physiologically active entities can be greatly enhanced by becoming bound to long lived blood components. The covalently bound entity may also serve as an antagonist or agonist of a particular binding proteins or as an enzyme inhibitor.

15 Claims, 1 Drawing Sheet

FIGURE 1

AFFINITY LABELING LIBRARIES WITH TAGGED LEAVING GROUP

RELATED APPLICATIONS

This application is a continuation-in-part application Ser. No. 08/714,754 filed Sep. 16, 1996 now abandoned.

BACKGROUND OF THE INVENTION

The advent of combinatorial chemistry has provided a platform for a wide variety of opportunities. The ability to produce large libraries of different compounds means that one can screen a large array of conformations, and charge distributions for their ability to bind to other compounds to act as agonists or antagonists, in binding to specific sites of a target protein, to investigate the conformation of a particular protein site, such as an enzymatic cleft or membrane channel protein, and the like.

Prior art libraries are cumbersome to screen. Difficulties arise when one attempts to identify a ligand which specifically interacts with a molecule of interest from those ligands which do not specifically interact with the molecule of interest.

Thus, there is a need to develop libraries which would provide affinity groups capable of interacting with a molecule of interest. Such libraries would be highly useful if they could simultaneously covalently bond an entity of interest to the molecule of interest to allow identification of the molecule while simultaneously releasing the affinity group for characterization and further study.

BRIEF SUMMARY OF THE INVENTION

Methods and compounds are provided for directed covalent bonding of an entity to a target molecule, even site, in the presence of a plurality of chemically reactive competitive sites. Also, screening techniques are provided for identifying affinity labels for directing the entity to the target molecule. The screening technique employs a library of compounds wherein the compounds have dual functions, (1) to provide non-covalent binding affinity for a specific target site and (2) to release a tagged leaving group when a chemically reactive group on the compound covalently bonds to a reactive functionality at the target site. As such, one may combine a library of compounds with a target. By monitoring the rate at which the leaving groups are released, one can determine which leaving groups have the higher binding affinity for the target molecule. If one wishes to identify a particular region of the target molecule for binding, the members of the library which are assayed with the target compound may be individually screened, and the preferred bonding sites for the individual members determined by analysis of the product. Targets may be host derived or foreign. Host targets include cells and blood compounds present in undesirable concentrations, such as auto-, allo- or xenoreactive white cells, i.e. leukocytes, including macrophages, infected cells, platelets, tumorous cells, and overexpressed cytokines and hormones. Foreign targets include toxins, poisons, drugs of abuse, pathogenic infectious microbes, or the like.

The identified compounds can find use in enhancing the in vivo lifetime of a physiologically active entity, by selectively bonding the physiologically active entity to long lived blood component target sites in vivo. The identified compounds may also find use for altering the activity of an enzyme, including as enzyme inhibitors, for example, by providing steric hindrance at the enzyme active site, or as receptor agonists or antagonists.

The invention is further directed to combinatorial libraries wherein the library has the general structure: Biotinyl-SPhCO-A where SPhCO is a p-thiobenzoyl group and A is a moiety which includes at least one amino acid. The moiety A typically ranges from 1–20 amino acids, most typically amino acids. The moiety A can be one or more synthetic amino acid including β-alanine, γ-aminobutyrate, O-methyl-substituted threonine, O-methyl-substituted serine, and O-methyl-substituted tyrosine.

The invention is further directed to methods of screening the combinatorial libraries of the invention. These methods typically include the steps of a) incubating a plurality of affinity molecules with a target moiety wherein each affinity molecule includes i) an affinity group including an oligopeptide and ii) a reactive functionality selected from the group including: carboxy, phosphoryl, acyl, phosphinyl, phosphonyl, imine, thioimine, ester, thioester and disulfide groups; b) binding the affinity group to the target molecule; c) forming a covalent bond between the reactive functionality and the target molecule; d) releasing the affinity group from the reactive functionality and the target molecule; and e) identifying the affinity molecule.

DETAILED DESCRIPTION OF THE INVENTION

In accordance with the subject invention, compounds are screened and identified for directing covalent bonding to a particular target molecule. The compounds find particular use in covalently bonding an entity to a specific target molecule in the presence of a plurality of chemically reactive competitive sites on other molecules, so as to reduce the amount of non-random bonding in the mixture. Normally, the enhancement will be at least about a factor of 1.5 over totally random bonding as determined by comparison to that bonding which occurs with a compound that exhibits no increased specificity for any particular target molecule or site over any other target molecule or site, more usually at least about a factor of 2, preferably by a factor of 5, and more preferably by a factor of 10. Although bonding may be specifically directed toward a particular target molecule, rarely would one anticipate that bonding would be solely to the target molecule(s).

Targets may be host derived or foreign. Host targets include cells and blood compounds present in undesirable concentrations, such as auto-, allo- or xenoreactive white cells, i.e. leukocytes, including macrophages, infected cells, platelets, tumorous cells, and overexpressed cytokines and hormones. Foreign targets include toxins, poisons, drugs of abuse, pathogenic infectious microbes, or the like.

Targets may be cellular, e.g. a mobile cell, such as an erythrocyte or platelet, namely, anuclear cells, or a fixed cell, such as an endothelial cell; or soluble or mobile proteins which are present in the blood for extended periods of time and are present in a minimum concentration of at least about 0.1 μg/ml. Proteins which fulfill this concentration requirement include, serum albumin, transferrin, ferritin and immunoglobulins, particularly IgM and IgG. Host derived cellular targets further include, (with parenthetical clinical indication): T cell or subsets, such as αIFN+, CD4+, CD8+, LFA1+, etc., cells (autoimmune disease, alloreactivity, xenoreactivity and inflammation), B cells or subsets such as pre-B cells, CD5+, IgE+, IgM+ etc. (B cell lymphoma, xenograft, autoimmunity, anaphylaxy), leukocytes, such as macrophages and monocytes (inflammation, myelomonocytic leukemia), other leukocytes such as neutrophils, basophils, NK cells, eosinophils, or allo- or xeno-reactive leukocytes, etc. (inflammation, anaphylaxis, transplant rejection), stem cells such as CD34+ cells (polycythemia), fetal red cells, such as Rh+ red cells (prophylaxis of anti-Rh immunization after pregnancy in a Rh– mother), malignant cells (malignancies; CALLA) or infected cells, particularly retroviral, e.g. HIV, infected host cells, or the like.

Host derived non-cellular targets include soluble HLA, class I and class II, and non-classical class I HLA (E, F and G) for modulating immunoregulation, soluble T or B cell surface proteins, cytokines, interleukins and growth factors such as IL1, 2, 3, 4, 6, 10, 13, 14 and 15, soluble IL2 receptor, M-CSF, G-CSF, GM-CSF, platelet growth factors, alpha, beta, and gamma-interferons, TNF, NGFs, arachadonic acid metabolites such as prostaglandins, leukotrienes, thromboxane and prostacyclin for cardiovascular diseases, immunoglobulins such as total IgE for anaphylaxy, specific anti-allergen IgE, auto or allo-antibodies for autoimmunity or allo- or xenoimmunity, Ig Fc receptors or Fc receptor binding factors, carbohydrates (gal), natural antibodies involved in allo- or xenorejection, erythropoietin, angiogenesis factors, adhesion molecules, MIF, MAF, complement factors (classical and alternate pathways, including regulatory factors), PAF, ions such as calcium, potassium, magnesium, aluminum, iron, etc, enzymes such as proteases, kinases, phosphatases, DNAses, RNAses, lipases and other enzymes affecting cholesterol and other lipid metabolism, esterases, dehydrogenases, oxidases, hydrolases, sulphatases, cyclases, transferases, transaminases, atriopeptidases, carboxylases and decarboxylases and their natural substrates or analogs, superoxide dismutase, hormones such as TSH, FSH, LH, thyroxine (T4 and T3), renin, insulin, apolipoproteins, LDL, VLDL, cortisol, aldosterone, estriol, estradiol, progesterone, testosterone, dehydroepiandrosterone (DHEA) and its sulfate (DHEA-S), calcitonin, parathyroid hormone (PTH), human growth hormone (hGH), vasopressin and antidiuretic hormone (ADH), prolactin, ACTH, LHRH, THRH, VIP, cathecolamines (adrenaline, vanillylmandelic acid, etc.), bradykinins and corresponding prohormones, metabolites, ligands or natural cell or soluble receptors thereof, cofactors including atrionatriuretic factor (ANF), vitamins A, B, C, D, E and K, serotonin, coagulation factors, e.g. prothrombin, thrombin, fibrin, fibrinogen, Factor VIII, Factor XI, Willebrand factor, plasminogen factors, e.g. plasmin, complement activation factors, LDL and ligands thereof, uric acid, etc. In some instances one may provide specific effects associated with complement, by having inhibitors such as DAF, CD59, etc., compounds regulating coagulation, such as hirudin, hirulog, hementin, TPA, etc. or other compounds, such as tissue factor, nucleic acids for gene therapy, etc., compounds which are enzyme antagonists, compounds binding ligands, such as cytokines, hormones, inflammation factors (PAF, complementation factors), etc.

Foreign targets include drugs, especially drugs subject to abuse such as heroin and other opiates, PCP, barbiturates, cocaine and derivatives thereof, benzodiazepins, ecstasy, etc., poisons, toxins such as heavy metals like mercury and lead, chemotherapeutic agents, paracetamol, digoxin, free radicals, arsenic, bacterial toxins such as LPS and other gram negative toxins, Staphylococcus toxins, Toxin A, Tetanus toxins, Diphtheria toxin and Pertussis toxins, plant and marine toxins, snake and other venoms, virulence factors, such as aerobactins, radioactive compounds or pathogenic microbes or fragments thereof, including infectious viruses, such as hepatitis A, B, C, E and delta, CMV, HSV (types 1, 2 & 6), EBV, varisella zoster virus (VZV), HIV-1, -2 and other retroviruses, adenovirus, rotavirus, influenzae, rhinovirus, parvovirus, rubella, measles, polio, reovirus, orthomixovirus, paramyxovirus, papovavirus,: poxvirus and picornavirus, prions, plasmodia tissue factor, protists such as toxoplasma, filaria, kala-azar, bilharziose, entamoeba histolitica and giardia, and bacteria, particularly gram-negative bacteria responsible for sepsis and nosocomial infections such as *E. coli*, Acynetobacter, Pseudomonas, Proteus and Klebsiella, but also gram positive bacteria such as staphylococcus, streptococcus, etc. Meningococcus and Mycobacteria, Chlamydiae, Legionnella and Anaerobes, fungi such as Candida, *Pneumocystis carini*, and Aspergillus, and Mycoplasma such as Hominis and *Ureaplasma urealyticum.*

The compounds to be screened will, for the most part, have the following formula: Biotinyl-SPhCO-A where SPhCO is a p-thiobenzoyl group and A is a moiety which typically includes at least one amino acid.

For the most part, moiety A will be an affinity group that is oligomeric and, therefore, various types of affinity groups which find use include, for example, oligopeptides, oligonucleotides, oligosaccharides, combinations thereof, or the like. Generally, the affinity groups represented in any particular library will be of a common type. Oligomeric affinity groups are readily synthesized as a combinatorial library, so that the synthetic chemistry is substantially repetitive with the addition of each monomer unit to the growing oligomer. Also, methods will be available for analyzing the composition and/or sequence of the oligomeric affinity group. Alternatively, the affinity group may comprise small synthetic organic molecules having a molecular weight of at least about 200, and not more than about 5,000, generally ranging from about 250 to 2,000.

Generally, the oligomers employed will have at least 3 monomeric units, more usually at least 4 monomeric units, and usually fewer than 20 monomeric units, more usually fewer than 12 monomeric units, preferably fewer than 10 monomeric units and more preferably in the range of about 4–8 monomeric units. With regard to the affinity groups represented in the library, one or more monomeric units of the oligomer may remain constant, thereby providing a mechanism for reducing the overall complexity of the combinatorial library. The monomer units comprising the oligomeric affinity group may be naturally occurring or synthetic, generally being from about 2 to 30 carbon atoms, usually from about 2 to 18 carbon atoms and preferably from about 2 to 12 carbon atoms.

If the affinity group is an oligopeptide, the amino acid monomers may be naturally occurring or synthetic. Conveniently, the naturally occurring L-α-amino acids will be used, although the D-enantiomers may also be employed.

While the amino acid monomers of the oligomer may be any one of the 20 naturally occurring amino acids in either the L- or D-configuration, the amino acids employed will preferentially be free of reactive functionalities, particularly reactive functionalities which would react with the reactive functionality (R) of the affinity label compound. Therefore, the amino acids which are used will usually be free of reactive amino groups, A frequently also being free of thiol groups. Of particular interest are such amino acids as alanine (A), glycine (G), proline (P), valine (V), serine (S), phenylalanine (F), isoleucine (I) and leucine (L) or uncharged polar amino acids like methionine (M). Other amino acids which may find use include other aromatic amino acids, such as histidine (H), tryptophan (W), and tyrosine (Y) or arginine (R), glutamate and aspartate.

The amino acid monomers of the oligomeric affinity group may also be synthetic. Thus, any unnatural or substituted amino acids of from 4 to 30, usually from 4 to 20, carbon atoms may be employed. Of particular interest are the synthetic amino acids β-alanine and γ-aminobutyrate or functional group protected amino acids such as O-methyl-substituted threonine (T), serine (S), tyrosine (Y), or the like.

Amino acids which find use may have the carboxyl group at a site other than the terminal carbon atom, may have the amino group at a site other than the α-position or may be substituted with groups other than oxy, thio, carboxy, amino or guanidino, e.g. cyano, nitro, halo, particularly fluorine, oxo, inorganic acyl groups, etc.

Synthetic amino acids may also be monosubstituted on nitrogen as in peptoids, which are oligomers of N-substituted glycine residues. N-substituted amino acids which find use will have an N-substituent of from about 1 to 8, usually 1 to 6 carbon atoms, which may be aliphatic, alicyclic, aromatic or heterocyclic, usually having not more than about 3 heteroatoms, which may include amino, either tertiary or quaternary, oxy, thio, and the like.

Oligopeptides may be constructed by employing standard Merrifield solid phase synthetic methods, manually or by using an automated peptide synthesizer, standard protection chemistry (e.g., t-Boc or Fmoc chemistry) and resins (e.g., 4-methyl benzhydryl amine Rink Amide resin). Successive rounds of deprotection of the terminal amino group and coupling of amino acid monomers, followed by deprotection and cleavage of peptides from resins results in the synthesis of oligopeptides of the desired sequence and length. Additionally, liquid phase peptide synthesis is well known in the art and may also be employed.

If the amino acid monomers employed are N-substituted glycine residues, monomers may incorporate t-butyl-based side chain and 9-fluorenylmethoxycarbonyl α-amine protection. (See, for example, Gordon et al., J. of Medicinal Chemistry (1994) 37, 1387–1385, and references cited therein). Controlled oligomerization of the N-substituted monomers may be performed manually and/or robotically with in situ activation by either benzotriazol-1-yloxytris(pyrrolidino)-phosphonium hexafluorophosphate or bromotris(pyrrolidino) phosphonium hexafluorophosphate. Additional steps may follow standard automated peptide synthesis protocols using α-(9-fluorenylmethoxycarbonyl)amino acids.

If the affinity group includes an oligonucleotide, either naturally occurring or synthetic nucleotide monomers may be employed. Particularly, for synthetic nucleotides, the phosphate or sugar groups may be modified where phosphate may be substituted by having the oxygen atoms replaced with sulfur or nitrogen, the phosphate group may be replaced with sulfonate, amide etc., the ribose or deoxyribose may be replaced with 5 to 6 carbon atom sugars such as arabinose, fructose, glucose, or the like, and the purines and pyrimidines may be modified by substitution on nitrogen, with alkyl or acyl, may employ different ring structures, may have nitrogen replaced by oxygen, or vice versa, and the like.

If the affinity group includes an oligosaccharide, the oligosaccharide will usually have from 4 to 6 monomeric units which may be linear or branched, comprised of sugars of from 5 to 8 carbon atoms. Various modifications of known oligosaccharides may be employed, particularly where one is interested in binding to lectins or adhesion molecules.

Combinatorial libraries of affinity groups may be prepared in accordance with conventional ways for producing combinatorial libraries, particularly using a solid support and adding the monomeric components in a stepwise manner. See, for example, U.S. Pat. Nos. 4,883,092; 5,010,175; 5,182,366 and 5,270,170 and PCT application Nos. WO 92/00091; WO 92/09300; WO 93/06121; WO 93/20242; WO 94/06451; WO 94/06291 and WO 95/28640, as exemplary of a much larger literature of techniques. Preferably, the synthetic chemistry is substantially repetitive with the addition of each monomer unit to the growing oligomer.

Initially, one will have a combinatorial library of compounds having varying affinity groups which are to be screened for their affinity to a target molecule or site. Generally, the library will have compounds representing at least 50 different affinity groups, frequently 100 different affinity groups, usually at least about 500 different affinity groups, preferably at least about 1000 different affinity groups, and may be 10,000 or more different affinity groups, although usually the libraries will have 5,000 or fewer different affinity groups. The library may have greater proportions of one compound over other compounds, but desirably the relative concentrations will differ by less than about 50%, preferably less than about 25%. For the screening process, the libraries may be divided into smaller units, which will generally range from about 5 to 1,000, frequently from about 5 to 500, usually from about 10 to 500 moieties and more usually from about 10 to 250. The source of the affinity groups may be any convenient source including combinatorial libraries, natural products, stored synthetic compounds, and the like.

Biotin is one example of an entity which includes any of a wide variety of biologically active or non-biologically active compounds which find application for bonding to targets in a complex mixture. Entities are such that they perform the desired function in the environment in which they become covalently bonded. For the most part, that environment will be an aqueous environment, usually serum or the interstitium. For use as drugs, the entity may be an agonist, an antagonist, a specific binding compound, an enzyme inhibitor (where the enzyme may be either soluble or membrane bound), a metal chelator, a factor supplement, a molecular scavenger, such as vitamin E, or the like. More specifically, the entity may include thrombin inhibitors, such as argatroban (for example see Ser. No. 08/674,315 now U.S. Pat. No. 5,840,733, which is hereby incorporated by reference.), renin inhibitors, ACE inhibitors, inhibitors of the coagulation and complement cascade, serine proteases, $\alpha_v\beta_3$ antagonists, GPIIb/IIIa antagonists, CRF antagonists, or the like.

Thus, the nature of the entity may be varied widely, depending upon its purpose. In one application, the entity may serve as a physiologically active compound, where the purpose of the subject compound is to bond the physiologically active compound to a long lived blood component. The affinity label serves to enhance the amount of the entity which is bound to a particular target site. For the most part, when used as a physiologically active compound, the subject compound will be combined with a complex mixture, such as blood, cells, tissue, or the like. Particularly, the subject compounds may be administered in vivo as described in co-pending application Ser. No. 08/237,346, now U.S. Pat. No. 5,612,034, whose disclosure is incorporated herein by reference. When used with blood, the primary targets will be immunoglobulins, red blood cells, particularly glycophorin proteins of the red blood cells, serum albumin, and platelets, however, other target sites are available.

In another application, the entity may be a compound which allows the diagnostic visualization of specific sites or compartments within the body by employing such diagnostic techniques as positron emission tomography (PET), computerized tomography (CT), single photon emission computerized tomography (SPECT), magnetic resonance imaging (MRI), nuclear magnetic imaging (NMI), fluoroscopy, ultrasound, etc. For such applications, the entity may comprise such things as contrast agents, radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{11}$C, or the like, fluorescently labeled compounds, etc. Such entities are also useful for identifying the presence of particular target sites in a mixture, to label molecules in a mixture, and the like. Various examples are found in U.S. application Ser. No. 08/588,912 now abandoned assigned to the Assignor of this application and hereby incorporated by reference.

In yet another application, the entity may be chosen such that it functions to sterically hinder or alter the binding specificity of a specific target binding protein. Such entities may take many forms which are readily determinable by those skilled in the art, and include various chemical groups, including acetyl, methyl, ethyl, propyl, and the like. Such entities may also comprise amino acids, oligomeric structures which themselves serve to provide binding affinity for the target molecule, much like the affinity groups described supra or small molecules such as biotin, or the like. Such entities find use, for example, for inhibiting the ability of a binding protein to bind to its substrate and for inactivating cell membrane proteins, such as channels, enzymatic proteins, specific receptors, and the like. Such entities may also serve a research purpose, for example, in allowing the dissection of the function of a variety of surface membrane proteins or for the identification and/or purification of the labeled target molecule.

In each of the above applications, covalent bonding of the entity serves to affect the biological function of the target molecule to which it is bound. Thus, by employing the subject compositions, one may modify the nature of the target molecule, change the characteristics of the target molecule, allow for the identification and/or isolation of the target molecule, etc.

The affinity group can be bonded to the entity (E) through a unit, usually a multicomponent unit, where the unit will comprise a chemically reactive functionality which will react with a reactive functionality at the target site to form a covalent bond. Covalent bond formation at the target site, in turn, results in covalently bonding the entity to the target site with concomitant liberation of the affinity group.

The compositions of the invention will include a reactive functionality, such as SPhCO. The reactive functionality, will generally be stable in an aqueous environment and will usually be carboxy, phosphoryl, or convenient acyl group, either as an ester or a mixed anhydride, or an imidate, thereby capable of forming a covalent bond with an amino group at the target site to form an amide or amide derivative. For the most part, the esters will involve phenolic compounds, or be thiol esters, alkyl esters, phosphate esters, or the like.

While the reactive functionality is usually chosen to react with an amino group at the target site, other functionalities at the target site may be exploited. For example, the reactive functionality may comprise various phosphinyl or phosphonyl derivatives for the bonding to available hydroxyl functions at the target site or may comprise an imine, thioimine or disulfide for bonding to thiol residues.

The composition of the invention may include a separator or connector between the entity and the affinity group. The separator or connector may provide for synthetic convenience, particular physical characteristics of the total composition, e.g. water solubility, reduced non-specific binding, the group bonded to the reactive functionality to provide an active ester, mixed anhydride, imidate, phosphate derivative, imine, thioimine, or the like. For the most part, the separator or connector, when other than a bond, will have from about 2–30 carbon atoms, and from about 0–10, more usually 1–8 heteroatoms, which for the most part will be O, N, P, S, and halogen. The particular separating group may not be critical to this invention, as indicated being selected based on the nature of the entity and the affinity group to provide convenient characteristics for the molecule. Of particular interest, where the separator or connector component is involved with the reactive functionality R, is to have an aromatic carboxylic acid derivative, so that the heteroatom of the reactive functionality is bonded directly to an aromatic carbon atom. Alternatively, one may have a carboxysuccinimidyl, sulfosuccinimidyl, or thiosuccinimidyl, for insertion as the separating group.

The connector or separator may have various functions in relation to the entity, in enhancing the availability of the entity by providing for enhanced water solubility in relation to the entity, by providing for a useful linking group between the entity and the adjacent unit, by enhancing the desired activity of the entity, for providing for the manifestation of the entity's desired function, or the like. For the most part, the connector will be bifunctional of from about 1–20 atoms in the chain, which atoms may be carbon, nitrogen, oxygen, sulfur, phosphorus, and the like. The connector may be alkylene groups, generally of from 2–16, more usually of from 1–25 carbon atoms, polyoxyalkylene groups, where the alkylene groups will be of 2–3 carbon atoms, and having from 1–8, more usually of from about 1–6 units, an amino acid, including alpha and omega amino acids, or oligopeptide having from 1–8, usually 1–6 amino acids, where the amino acids may be polar or non-polar, charged or uncharged, aliphatic, alicyclic, aromatic or heterocyclic, naturally occurring or synthetic.

As is evident from the above, the various units of the affinity label compound will be selected in relation to the nature of the entity and the affinity group, particularly the entity. Thus, the components of the multicomponent unit will be selected in relation to the use of the compound, and the effect of the components on the intended use of the compound.

For identification of affinity label members of the library having increased affinity for a particular target site relative to other members of the library, as indicated previously, depending upon the size of the library, all or a portion of the members of the library may be combined with the pure target compound in an appropriate reaction medium. The medium will vary widely, depending upon the nature of the target compound, and the environment in which the subject affinity label compounds will be used for bonding to the target compound. For the most part, the media will be polar, particularly aqueous, and may be buffered or otherwise modified to as to more closely mimic the ultimate environment in which the subject compounds will be used. The concentrations of the target compound and the library members may be varied widely, usually being determined empirically, so as to optimize the differentiation between the various members of the library. Generally, for screening purposes, concentrations of the target compound will be in the range of about 0.05 to 5 µM, preferably in the range of about 0.1 to 1.0 µM, while concentrations of the library will vary in the range of about 10 to 150 µM, preferably in the range of from about 50 to 100 µM and more preferably in the range of from about 75 to 85 µM.

The temperature of the reaction may be varied over a broad range compatible with the stability of the components of the system, frequently being room temperature or the temperature of the environment in which the subject compounds will be used. To the extent that the subject compositions will be used physiologically, the temperature will generally be in the range of about 34–40° C., more usually about 37° C.

The determination of affinity for the target exhibited by the various affinity label members of the library may be made by determining the composition of the liberated affinity groups at a single time point or a plurality of time points after the reaction is initiated. For the most part, those affinity groups which are liberated the earliest after the reaction is initiated are those which exhibit the greater binding affinity for that target site. Usually, the reaction will be allowed to proceed until there is a sufficient population of liberated affinity groups to allow for their ready determination and differentiation. The affinity label leaving groups may be analyzed by any convenient means, including mass spectrometry, gel electrophoresis, chromatography, e.g. HPLC, TLC, or the like, where if appropriate, the separated components may then be sequenced. Where a plurality of aliquots of the library used, those sequences demonstrating preferred affinities may then be combined in a subsequent determination for direct comparison.

The subject affinity label compounds will be synthesized in accordance with conventional ways. Synthesizers are commercially available for synthesizing oligonucleotides and oligopeptides. See the references cited above. Various conventional chemistries may be employed. Depending upon the nature of the functional group, the separator, the connector, and the entity synthetic strategies will be devised which allow for synthesis of the molecule at reasonable yields, and without the formation of complex mixtures. The particular synthetic strategy will be determined empirically, and on a case by case basis. Methods for combining various compounds are well known in the literature, and can be employed with advantage. Where precursors are known to the entity, particularly prodrugs for drugs, the prodrugs will frequently indicate the site for attachment and the nature of a linking group. Where prodrugs are not available, the physiologically active molecule may be modified stepwise at different sites, and the activity of the resulting compound determined.

The subject affinity label compounds, when administered physiologically, will usually be administered as a bolus, but may be introduced slowly over time by transfusion using metered flow, or the like. Alternatively, although less preferable, blood may be removed from the host, contacted with the affinity label compound ex vivo, and returned to the host. The affinity label compounds will be administered in a physiologically acceptable medium, e.g., deionized water, phosphate buffered saline, saline, mannitol, aqueous glucose, alcohol, vegetable oil, or the like. Usually, a single injection will be employed although more than one injection may be used, if desired. The affinity label compounds may be administered by any convenient means, including syringe, catheter, or the like. The particular manner of administration will vary depending upon the amount to be administered, whether a single bolus, sequential, or continuous administration, or the like. Administration will be intravascular, where the site of introduction is not critical to this invention, preferably at a site where there is rapid blood flow, e.g., intravenously, peripheral or central vein. The intent is that the compound administered be effectively distributed in the vascular system so as to be able to react with target molecules therein.

The dosage of the affinity label compound will depend upon the entity being employed and will, therefore, be dependent on the adverse effects of the entity of interest, if any, the time necessary to reduce the unbound concentration of the affinity label compound present in the vascular system, the indication being sought, the sensitivity of the compound to destruction by vascular components, the route of administration, and the like. As necessary, the dosage of affinity label compound may be determined empirically, initially using a small multiple of the dosage normally administered, and as greater experience is obtained, enhancing the dosage. Dosages will generally be in the range of 1 ng/Kg to 10 mg/Kg, usually being determined empirically in accordance with known ways, as provided for in preclinical and clinical studies.

The following examples are offered by way of illustration, and not by way of limitation.

EXPERIMENTAL

1. Construction of p-Thiobenzoic-acid Containing Affinity Labeling Libraries An affinity labeling library with tagged leaving groups and having a p-thiobenzoic acid residue as a separator was designed and constructed. The structure of the affinity labeling library members is described as follows:

Biotinyl-SPhCO—$O_1$—$O_2$—$X_1$—$X_2$—B—$NH_2$ (81 wells, 81 compounds/well)

In the above described structure, $X_1$ and $X_2$ represent that all of the 9 selected L-amino acids appear in a well, $O_1$ represents that only one of the 9 selected L-amino acids appear in a well, $O_2$ represents that only one of the 9 selected D-amino acids appears in a well, and B represents that only one of the 9 selected L-amino acids appears in all 81 wells of a set. Biotinyl serves as the "entity" which becomes covalently bound to the target protein. The "SPhCO" represents the p-thiobenzoyl acid separator between the biotinyl "entity" and the oligomeric tagged leaving group.

Biotin, also known as 2'-keto-3,4-imidazolido-2-tetrahydrothiophene-n-valeric acid, is represented by the following structure:

Biotin

Biotinyl is represented by the following structure:

Biotinyl

Thiobenzoyl is represented by the following structure:

thiobenzoyl

Fluorenylmethyl thio benzoyl (Fm—S—Ph—$CO_2H$) is represented by the following structure:

Fm-SPh-CO2H

The precursor for Fm—S—Ph—$CO_2H$, 9-fluorenylmethyl chloide (Fm—Cl) was synthesized as follows. A solution of 25.0 g of 9-fluorenmethanol (127 mmol, ALDRICH® Chemical Company was refluxed with 150 ml of thionyl chloride. for 30 minutes. The excess thionyl chloride was a removed by distillation and the residue distilled at reduced pressure, then crystallized from ethanol two times to afford 19.2 g of 9-fluorenylmethyl chloride (89.4 mmol, 70%) as a pale yellow solid.

Fm—S—Ph—$CO_2H$ was prepared as follows: To a 0° C. suspension of 3.40 g of 4-mercaptobenzoic acid (85%, Toronto Research Chemicals) (18.7 mmol) in 60 mL of N,N-dimethylformamide (DMF) was added 4.00 g of 9-fluorenylmethyl chloride (Fm—Cl) (Bodansky, M.; Bednarek, M. A. Int. J. Pept. Protein Res. 1982, 20, 434) (18.7 mmol) and 6.9 mL of diisopropylethylamine (37.4 mmol). The reaction was allowed to slowly warm to RT where it stirred for 16 h. The cloudy yellow-brown solution was washed with hexanes (3×50 mL), diluted with 50 mL of 1 M HCl and extracted with ethylacetate (3×50 mL), which were washed with 50 mL of saturated aqueous NaCl, dried with anhydrous $MgSO_4$, filtered, and concentrated via rotary evaporation to afford a yellow-brown oil. This was then dissolved in 20 mL of MeOH, cooled to −20° C. and the resulting crystals were collected by filtration, washed with ice cold MeOH and dried to afford 5.59 g of Fm—S—Ph—$CO_2H$ as a white solid (13.0 mmol, 70%).

The 9 amino acids employed were carefully selected by considerations of the side chain functional groups and are listed in Table 1.

TABLE 1

| Code | Amino Acid | Category | Starting material |
|---|---|---|---|
| 1 | glutamic acid | acid | Fmoc-Glu(OtBu)-OH |
| 2 | glutamine | amide | Fmoc-Gln(Trt)-OH |
| 3 | arginine | base | Fmoc-Arg(Pmc)-OH |
| 4 | methionine | sulfide | Fmoc-Met-OH |
| 5 | serine | alcohol | Fmoc-Ser(tBu)-OH |
| 6 | tyrosine | phenol | Fmoc-Tyr(tBu)-OH |
| 7 | leucine | aliphatic | Fmoc-Leu-OH |
| 8 | phenylalanine | aromatic | Fmoc-Phe-OH |
| 9 | tryptophan | aromatic | Fmoc-Trp(Boc)-OH |

The D-amino acids, $O_2$ were introduced in order to prevent facile peptidyl cleavage in vivo and to maximize the affinity to the macromolecular targets.

In each set there are 81 wells and in each well there are 81 compounds while B is fixed. Such results in a library of 6561 total library members.

For example, when glutamic acid (E) was chosen to be the residue "B" in the above formula, the set 1 of combinatorial p-thiobenzoyl-containing affinity labeling libraries Biotinyl-SPhCO—$O_1$—$O_2$—$X_1$—$X_2$—E—$NH_2$ was tructed as follows:

The synthesis utilized Merrifield solid phase peptide synthesis methods and Fmoc chemistry. Rink amide resin was used to furnish amide at the C-terminus. A schematic illustration outlining the construction of this set of libraries described above is shown in FIG. 1.

Figure 1:
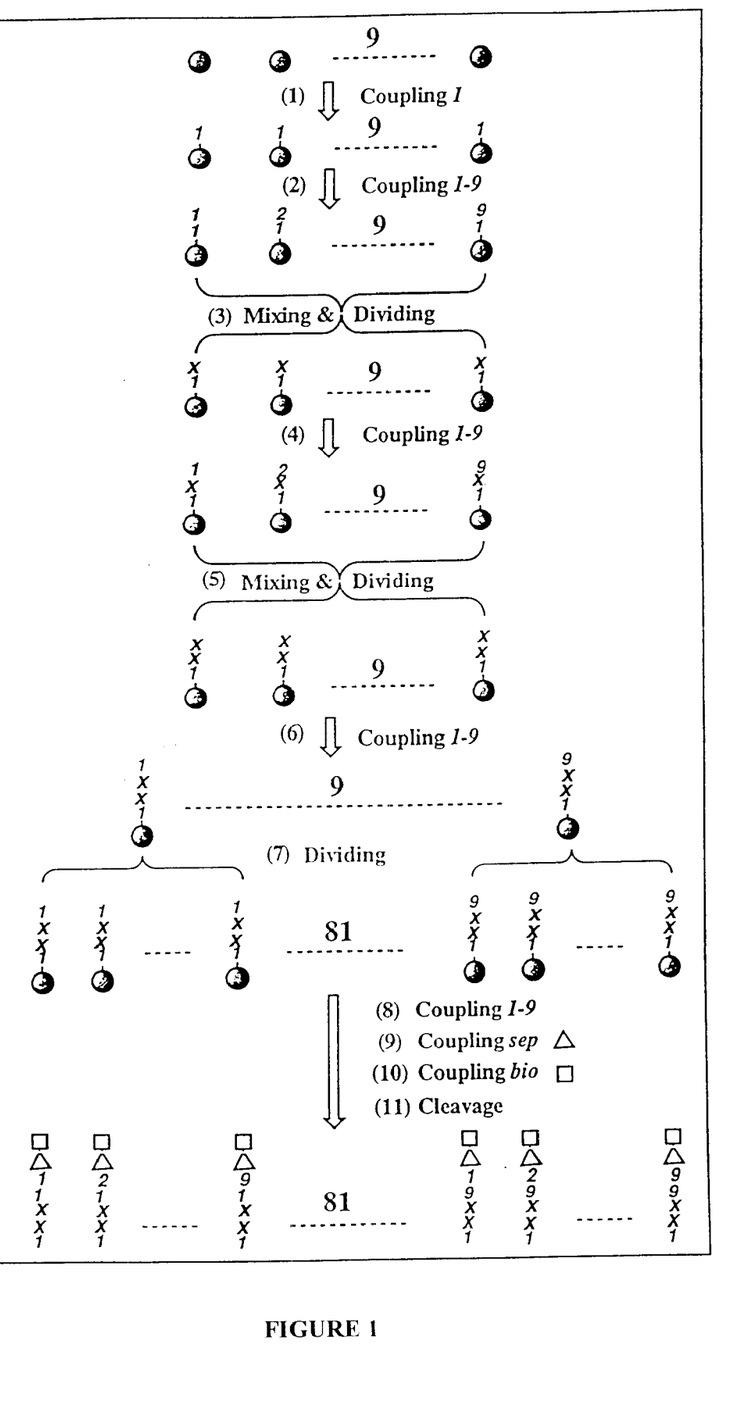
FIG. 1 is a schematic illustration of the construction of an affinity labeling library of the present invention.

In step (1) shown in FIG. 1, Fmoc-Glu(OtBu)—OH was coupled to an identical amount of resin support in all 9 reaction vessels after removal of the Fmoc protecting group on Rink amide resin.

Removal of the Fmoc group was performed by treating with 20% piperidine in N-methylpyrrolindin-one (NMP) twice, 2 minutes and 15 minutes, respectively at room temperature, followed by several NMP washes.

Coupling of the Fmoc-Glu(OtBu)—OH to the resin support was performed by adding to the resin in a reaction vessel with an N,N-dimethylformamide (DMF) solution of the amino acid (4 equivalents), O-benzotriazol-1-yl-N,N,N', N'-tetramethyl-uronium hexafluorophosphate (HBTU) (4 equivalents), 1-hydroxybenzotiazole (HOBt) (4 equivalents) and diisopropylethyl amine (DIEA) (8 equivalents). The reactions were allowed to proceed for 2 hours at room temperature. Completion of each reaction was monitored by a ninhydrin test to measure the extent of unreacted amino groups. The coupling reactions were repeated until the ninhydrin test for each reaction was negative. Once coupling was complete as evidenced by a negative ninhydrin test, the peptide resin in each of the nine separate reactions was washed repeatedly with DMF.

Before the second L-amino acids were coupled to an identical amount of resin bearing the same Fmoc protected amino acid (i.e., Fmoc-Glu(OtBu)—OH) in all 9 reaction vessels), the Fmoc protecting group was removed by treating with 20% piperidine in NMP twice, 2 minutes and 15 minutes, respectively, at room temperature, followed by several NMP washes.

As shown in step (2) of FIG. 1, each of the nine different Fmoc-protected L-amino acids shown in Table 1 were then individually linked to an identical amount of resin in all 9 reaction vessels. Coupling reactions were again carried out by adding to the resin in a reaction vessel with an DMF solution of the amino acid (4 equivalents), HBTU (4 equivalents), HOBt (4 equivalents) and DIEA (8 equivalents). The reactions were allowed to proceed for 2 hours at room temperature. Completion of each reaction was monitored by a ninhydrin test. The coupling reactions were repeated until the ninhydrin test for each reaction was negative. Once coupling was complete as evidenced by negative ninhydrin test, the peptidyl resin in each of the nine separate reactions was washed with DMF.

The result of this second round of coupling is the generation of nine equimolar independent and distinct pools of dipeptides linked to resin support. As shown in FIG. 1, since each of the nine independent and distinct pools contains one distinct dipeptide, there are now generated a total of 9 distinct dipeptides.

As shown in step (3) of FIG. 1, the resins from each of the nine independent and distinct pools generated in step (2) were mixed and then divided into identical pools. This gives rise to nine identical pools each consisting of nine distinct dipeptides linked to the resin support.

Before the third round of coupling, the Fmoc protecting group was removed by treating with 20% piperidine in NMP twice, 2 minutes and 15 minutes, respectively, at room temperature, followed by several NMP washes.

As shown in step (4) of FIG. 1, each of the nine different Fmoc-protected L-amino acids shown in Table 1 were individually linked to an identical pool of resin in all 9 reaction vessels. Coupling reaction were carried out as described above.

As shown in step (5) of FIG. 1, the resins from each of the nine independent and distinct pools generated in step (4) were mixed and then divided into identical pools. This gives rise to nine identical pools each consisting of eighty one distinct tripeptides linked to the resin support.

Before the fourth round of coupling, the Fmoc protecting group was removed by treating with 20% piperidine in NMP twice, 2 minutes and 15 minutes, respectively at room temperature, followed by several NMP washes.

As shown in step (6) of FIG. 1, each of the nine different Fmoc-protected amino acids shown in Table 1 were identically linked to an identical pool of resin in all 9 reaction vessels. In this round of coupling, unlike all of the other round of coupling, amino acids in the D-configuration are employed. Coupling reaction were again carried out as described above.

The results of this fourth round of coupling is the generation of nine equimolar independent and distinct pools of tetrapeptide linked to resin support. As shown in FIG. 1, since each of the nine independent and distinct pools contains eighty one distinct tetrapeptides, there are now generated a total of 729 distinct tetrapeptides.

As shown in step (7) of FIG. 1, each of the nine independent and distinct pools of tetrapeptides generated in step (6) were each divided in to a set of nine identical pools without mixing the pools before dividing. This gives rise to nine sets of identical pools (81 pools total) each containing 81 tetrapeptides. The step of splitting the pools without mixing allows for the identity of the fourth and fifth amino acids coupled to the resin to be defined. Before the fifth round of coupling, the Fmoc protecting group was removed by treating with 20% piperidine in NMP twice, 2 minutes and 15 minutes, respectively, at room temperature, followed by several NMP washes.

As shown in step (8) of FIG. 1, each of the nine identical pools in each of the nine sets of pools generated in step (7) was then coupled by one of the nine Fmoc-protected amino acids shown in Table 1. The coupling reaction were again carried out as described above.

The results of this fifth round of coupling is the generation of eighty one equimolar independent and distinct pools of pentapeptides linked to a resin support. As shown in FIG. 1, since each of eighty one independent and distinct pools contains eighty one distinct pentapeptides, there are now generated a total of 6561 distinct pentapeptides.

As shown in step (9) of FIG. 1, each of the eighty one independent and distinct pools generated in step (8) was then coupled by a common protected separator 4-(S-9-fluorenylmethyl ether) benzoic acid (Fm—S—Ph—CO$_2$H). Before the coupling of Fm—S—Ph—CO$_2$H, the Fmoc protecting group was removed by treating with 20% piperidine in NMP twice, 2 minutes and 15 minutes, respectively at room temperature, followed by several NMP washes.

Coupling reactions were carried out by adding to the resin in a reaction vessel with a DMF solution of S-fluorenylmethyl-p-thiobenzoic acid (4 equivalents), HBTU (4 equivalents), HOBt (4 equivalents) and DIEA (8 equivalents). The reactions were allowed to proceed for 2 hours at room temperature. Completion of each reaction was monitored by a ninhydrin test. The coupling reactions were repeated until the ninhydrine test fore each reaction was negative. Once coupling was complete as evidenced by a negative ninhydrin test, the peptidyl resin in each of the nine separate reactions was washed with DMF.

Before the last round of coupling, the fluorenylmethyl protecting group was removed by treating with 20% piperidine in NMP twice, 2 minutes and 10 minutes, respectively at room temperature, followed by NMP washes rapidly.

As shown in step (10) of FIG. 1, each of eighty one independent and distinct pools generated in step (8) was then coupled to biotin. Coupling reaction were carried out by adding to the resin in a reaction vessel with a DMF solution of biotin (5 equivalents), HBTU (5 equivalents), HOBt (5 equivalents) and DIEA (10 equivalents). The reactions were allowed to proceed for 2 hours at room temperature. The coupling reactions were repeated to ensure completion.

Finally, to complete the construction of the p-thiobenzoyl-containing affinity labeling libraries, as shown in step (11) of FIG. 1, the completely constructed affinity labeling libraries were cleaved from the resin component and purified. The cleavage and purification were performed as follows.

The peptidyl resin mixtures in each 81 independent and distinct pools generated in step (10) were dried. Each was then independently treated with trifluoroacetic acid (TFA)/H$_2$O (95/5, v/v) for 1.5 hours. The peptide/TFA solution was then precipitated then washed with ether. Following ether precipitation, the peptide solution was suspended in 0.045% TFA in water and lyophilized giving rise to the completely constructed and dried p-thiobenzoyl-containing affinity labeling library.

The final combinatorial p-thiobenzoyl-containing affinity labeling library is substantially stable under normal storage conditions as determined by mass spectral analysis.

2. Screening of Affinity Labeling Library

The screening of libraries that contain an entity which becomes covalently bonded to the target protein as a result of the affinity labeling reaction may be conducted in two sequential steps and serves as a specific example of a general method for detecting the existence of a covalent adduct. The first step of the screening process is the reaction of a given target protein with the affinity labeling library or portion thereof. These reactions are typically conducted at room temperature, although not exclusively so, in the wells of polypropylene 96-well plates. Specified wells contain the target protein that is typically present at a concentration between 0.1 and 1 $\mu$M in a buffered solution that is of an appropriate composition and pH for maintaining the native biological structure and function of the target protein. Labeling reactions are initiated by the addition of a solution of affinity labeling library members in DMSO to give typical concentrations of total library and DMSO of 80 μM and 2% (volume/volume), respectively. The labeling reactions are terminated at a specified time, which may be either as short as 5 seconds or longer than 1 hour, by the addition of a suitable quench reagent (i.e. hydroxylamine for quenching thioesters) that combines with unreacted library members to give forms of the library that no longer react with the target protein. Specified wells of the plate contain reaction mixtures that measure the amount of non-covalent binding of the entity to the target protein. These control reactions are conducted by first mixing the library with the quench reagent for a time sufficient to give forms of the library that do not react with the target protein and then subsequently adding the target protein.

The detection of the entity that is covalently bound to the target protein is the second step of the screen and uses-standard methodologies which are known in the art. For example, if the entity that becomes covalently bonded to the target protein is biotin, Enzyme-Linked-Immunoassays (ELISA's) can be employed to detect covalent bonding. Briefly, polystyrene 96-well plates can be coated with an antibody that specifically binds the target protein and modified forms thereof. A portion of each reaction mixture may then be transferred to the corresponding wells of the antibody-coated plate, and the binding of target protein to antibody allowed to ensue for approximately 2 hours. The plate is then emptied and 10 times filled with and emptied of phosphate buffered saline (PBS, 10 mM Pi, pH 7.4, 137 mM NaCl, 2.7 mM KCl). This washing procedure removes non-covalently bound biotin from the well. A solution containing the enzyme conjugate avidin-horse-radish peroxidase may then be added to the washed well, and the binding of avidin of the conjugate to biotin of the modified target molecule, which is bound to the antibody of the plate, is complete after 30 minutes. The plate may then be washed as described above, and hydrogen peroxide and orthophenyl diamine are added as substrates of the peroxidase enzyme to give a visual measure of the amount of conjugate present in each well; conjugate amount is proportional to the amount of modified target protein in the well. The optical densities of each well are measured, and the values obtained are recorded in a computer spreadsheet and analyzed.

While the ELISA method of screening that is described above is specific for biotin-containing proteins, the method is, in principle, applicable for measurement of any Affinity Labeling Library that results in the formation of a detectable adduct with any target biomolecule that can be sequestered at the surface of a 96-well plate.

It is evident from the above, that the subject invention provides an efficient approach to identifying affinity label compounds which can be used to direct a specific entity to a target site. Thus, the subject invention allows for marking specific targets, particularly proteins, for a wide variety of purposes. Where complex mixtures are involved, such as blood, one can provide for enhanced bonding to a specific component in the blood, more particularly, a specific site on the target. In this way, one may provide for specific targeting to mobile components, such as blood cells, e.g. erythrocytes and platelets, proteins, such as immunoglobulins, serum albumin, transferrin, and the like. In mixtures in culture, one may specifically inhibit an enzyme target, so as to prevent enzymatic interference with the culture. For example, one may provide for specific bonding to RNases to prevent degradation of RNA. One may inhibit specific hydrolases, oxidoreductases, or the like. Where one wishes to mark a particular target, one can provide for fluorescent, radioactive, or other entity, which may be detected.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A method for identifying an affinity molecule that binds and bonds to a target moiety, comprising:
   a) incubating a plurality of affinity molecules with said target moiety wherein each affinity molecule comprises:
      i) an affinity group comprising an oligopeptide; and
      ii) a reactive functionality selected from the group consisting of: carboxy, parathiobenzoyl, phosphoryl, acyl, phosphinyl, phosphonyl, imine, thioimine, ester, thioester, thiobenzoyl, and disulfide groups;
   b) non-covalently binding said affinity group to said target moiety;
   c) forming a covalent bond between said reactive functionality and said target moiety; thereby causing the release of said affinity group from said reactive functionality and said target moiety, and
   d) identifying said affinity group.

2. The method of claim 1 wherein said oligopeptide consists of the sequence $O_1$—$O_2$—$X_1$—$X_2$—B—$NH_2$ wherein $O_1$, $O_2$, $X_1$, $X_2$ and B are amino acids.

3. The method of claim 2 wherein one or more of said amino acids is a synthetic amino acid.

4. The method of claim 3 wherein said synthetic amino acid is selected from the group consisting of β-alanine, γ-aminobutyrate, o-methyl-substituted threonine, o-methyl-substituted serine, and o-methyl-substituted tyrosine.

5. The method of claim 2 wherein $O_1$, $X_1$, $X_2$ and B are L-amino acids and $O_2$ is a D-amino acid.

6. The method of claim 5 wherein said amino acids are selected from the group consisting of glutamic acid, glutamine, aspartic acid, asparagine, arginine, methionine, serine, tyrosine, leucine, isoleucine, alanine, glycine, threonine, valine, proline, phenylalanine and tryptophan.

7. The method of claim 1 wherein said affinity molecule further includes biotin.

8. The method of claim 1 wherein said reactive functionality is a para-thiobenzoyl group.

9. The method of claim 1 wherein said oligopeptide consists of between 1 and 20 amino acids.

10. The method of claim 1 wherein said oligopeptide consists of between 1 and 10 amino acids.

11. The method of claim 1 wherein said affinity molecule is a composition comprising:

Biotinyl-SPhCO—$O_1$—$O_2$—$X_1$—$X_2$—B—$NH_2$
   wherein $O_1$, $O_2$, $X_1$, $X_2$ and amino acids and SPhCO is parathiobenzoyl.

12. The method of claim 11 wherein one or more of said amino acids is a synthetic amino acid.

13. The method of claim 11 wherein said synthetic amino acid is selected from the group consisting of β-alanine, γ-aminobutyrate, o-methyl-substituted threonine, o-methyl-substituted serine, and o-methyl-substituted tyrosine.

14. The method of claim 11 wherein $O_1$, $X_1$, $X_2$ and B are L-amino acids and $O_2$ is a D-amino acid.

15. The method of claim 14 wherein said amino acids are selected from the group consisting of glutamic acid, glutamine, aspartic acid, asparagine, arginine, methionine, serine, tyrosine, leucine, isoleucine, alanine, glycine, threonine, valine, proline, phenylalanine and tryptophan.

* * * * *